United States Patent [19]

Sarrell et al.

[11] Patent Number: 4,580,570
[45] Date of Patent: Apr. 8, 1986

[54] ELECTRICAL THERAPEUTIC APPARATUS

[75] Inventors: Ivan D. Sarrell, Rising Fawn, Ga.; David B. Bley, Chattanooga, Tenn.

[73] Assignee: Chattanooga Corporation, Chattanooga, Tenn.

[21] Appl. No.: 223,318

[22] Filed: Jan. 8, 1981

[51] Int. Cl.[4] ............................................. A61N 1/32
[52] U.S. Cl. .................................. 128/421; 128/423 R
[58] Field of Search .................. 128/419 R, 741, 799, 128/420 A, 420 R, 421, 422, 423 R, 423 W

[56] References Cited

U.S. PATENT DOCUMENTS

| | | | |
|---|---|---|---|
| 1,999,729 | 4/1935 | Kinney | 128/423 |
| 2,295,585 | 9/1942 | Lindquist | 128/421 |
| 2,713,120 | 7/1955 | Mostofsky et al. | 128/423 X |
| 2,764,683 | 9/1956 | Paust et al. | 128/423 X |
| 2,808,826 | 10/1957 | Reiner et al. | 128/741 |
| 2,823,311 | 2/1958 | Bastir | 128/421 |
| 2,864,371 | 12/1958 | Parodi | 128/419 R |
| 3,055,372 | 9/1962 | Browner | 128/421 |
| 3,127,895 | 4/1964 | Kendall et al. | 128/422 |
| 3,329,148 | 7/1967 | Kendall | 128/422 |
| 3,565,080 | 7/1967 | Ide et al. | 128/422 |
| 3,648,708 | 3/1972 | Haeri | 128/422 |
| 3,791,373 | 2/1974 | Winkler et al. | 128/1 C |
| 3,800,800 | 4/1974 | Garbe et al. | 128/423 |
| 3,851,651 | 12/1974 | Icenbice, Jr. | 128/422 |
| 3,881,494 | 5/1975 | Paul, Jr. | 128/421 |
| 3,954,111 | 5/1976 | Sato | 128/422 X |
| 4,014,347 | 3/1977 | Halleck et al. | 128/422 |
| 4,068,669 | 1/1978 | Niemi | 128/908 X |
| 4,069,827 | 1/1978 | Dominy | 128/422 |
| 4,084,595 | 4/1978 | Miller | 128/422 |
| 4,095,602 | 6/1978 | Leveen | 128/419 R |
| 4,121,592 | 10/1978 | Whalley | 128/413 |
| 4,140,130 | 2/1979 | Storm | 128/404 |
| 4,174,706 | 11/1979 | Jankelson et al. | 128/741 |
| 4,177,819 | 12/1979 | Kofsky et al. | 128/422 |
| 4,185,640 | 1/1980 | Kastrubin et al. | 128/421 |
| 4,188,927 | 2/1980 | Harris | 128/303.14 |
| 4,197,851 | 4/1980 | Fellus | 128/422 |
| 4,200,108 | 4/1980 | Weigert | 128/419 R |
| 4,237,887 | 12/1980 | Gonser | 128/303.14 |

FOREIGN PATENT DOCUMENTS

| | | | |
|---|---|---|---|
| 0000477 | 2/1979 | European Pat. Off. | |
| 0746665 | 3/1956 | United Kingdom | 128/419 R |
| 0877029 | 9/1961 | United Kingdom | |
| 1129142 | 10/1968 | United Kingdom | |

Primary Examiner—Kyle L. Howell
Assistant Examiner—Angela D. Sykes
Attorney, Agent, or Firm—Bell, Seltzer, Park & Gibson

[57] ABSTRACT

A high voltage pulsed electrical stimulation apparatus is provided which is useful for a variety of therapeutic purposes, and which is operable in a number of different modes of operation, including a continuous mode wherein the current is continuously applied, a surge mode wherein the current is periodically interrupted, and a reciprocate mode wherein a continuous current is alternately directed to two separate electrodes. The apparatus includes provision for measuring and visually displaying the peak current of the pulses, which has been found to provide a very reliable indication of the effectiveness of the treatment. Also, the apparatus includes circuitry for balancing the current between the two electrodes in the reciprocate mode, and which does not interfere with the desired peak current measurement. Further, circuitry provided for effectively cushioning the initial application of current at the commencement of each surge of current when the apparatus is operated in the surge mode.

14 Claims, 7 Drawing Figures

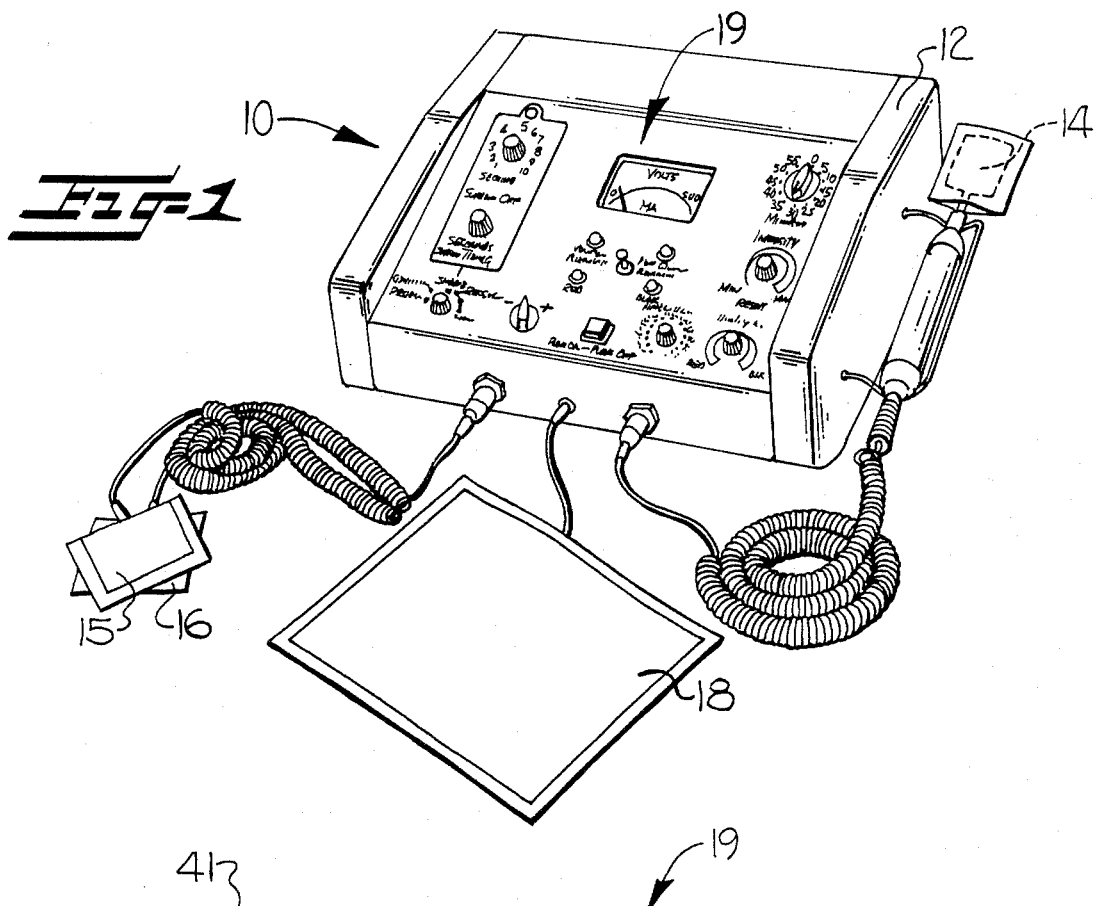
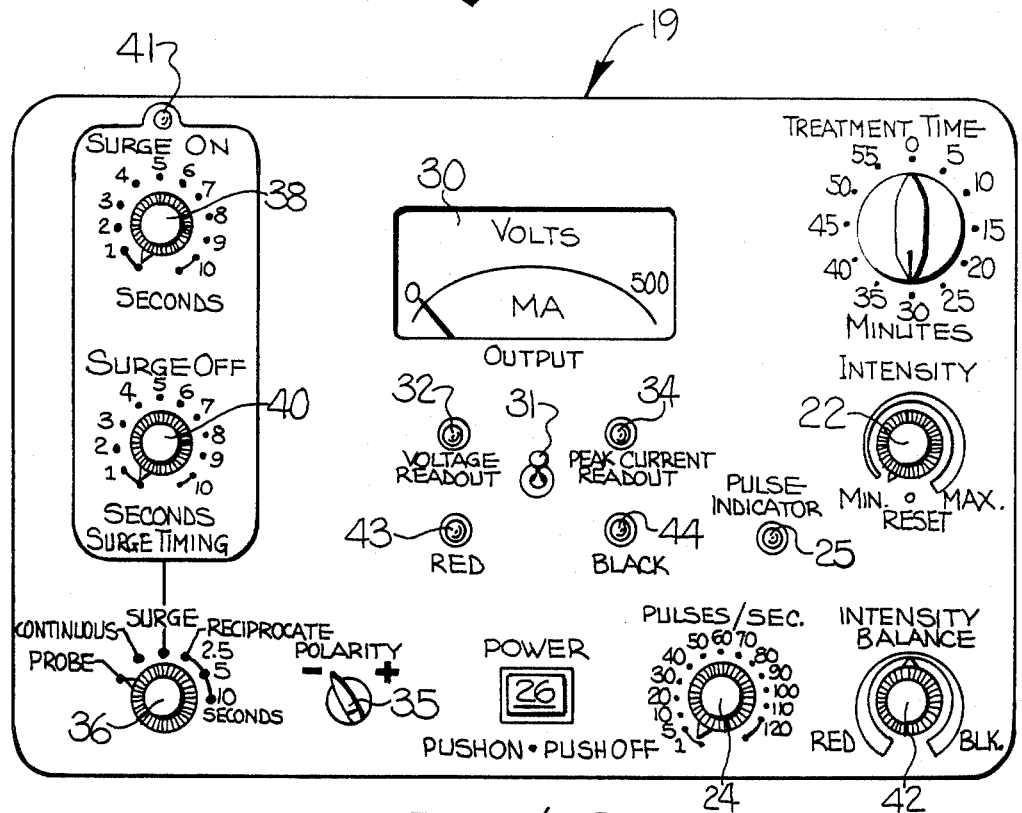

ELECTRICAL THERAPEUTIC APPARATUS

The present invention relates to an improved therapeutic apparatus adapted to provide electrical stimulation to the human body.

High voltage pulsed electrical stimulators are presently known and used which are adapted to provide electrical stimulation to the human body for a variety of clinical purposes, including the relief of muscle spasms, to reduce pain, to increase joint mobility, and to increase circulation. Such stimulators are typically designed to deliver a pulsating direct current, at a voltage above about 150 volts, and with the direct current in the form of pulses of very short duration, ranging between about 50 and 100 microseconds. The delivered current is further characterized by a high peak amperage, which may be as high as 300 to 400 milliamperes, which permits the current to penetrate to deep muscles or nerves.

In one presently marketed stimulator of the described type, a number of different electrodes are provided which can be selectively employed to provide several different functional modes of operation. More particularly, the above stimulator includes a hand held electrode or probe, which is used for locating muscle motor points, or locating and treating painful trigger points. In addition, the stimulator includes a pair of active flat electrodes which are adapted to be placed at spaced locations on the body. The current can be applied concurrently from the two electrodes, or it may be alternated between the two electrodes to cause alternating muscle contractions for effectively exercising the muscle, or increasing localized circulation. In order to monitor the current being applied to the body, the stimulator includes a voltage intensity meter, which visually indicates the treatment intensity with any selected mode of application.

The above described present stimulator also has provision for interrupting the pulsed current in a selected mode of application, to produce intermittent surges of pulsed current to the selected electrode. The application of such intermittent current is particularly useful in that the interrupted current is usually more effective in producing muscle contractions and exercise as compared to a continuous pulsed current.

When utilizing the above described apparatus in the mode wherein two electrodes apply the current to the body at spaced points, difficulty is often encountered in that the current delivered from the two electrodes may not be balanced, in view of the fact that the body has different conditions of electrical load or impedance at different points. Thus it is common for one of the electrodes to deliver a relatively high level of current which is uncomfortable to the patient, when the electrode is placed on a point of low impedance. Such imbalance is uncomfortable to the patient, particularly when the unit is operated so that the current is reciprocated between the two electrodes, and the desired therapeutic function may not be achieved.

The above described present apparatus is also deficient in that the therapist must rely on the patient reaction to determine whether the placement position of an electrode is effective, and patient reaction is sometimes difficult to detect and may not be totally reliable. Still further, difficulties are often encountered with the present apparatus when operated in the interrupted current or surge mode, since the initial application of the current at the commencement of each surge may produce a sudden sensory shock which is uncomfortable to the patient, and which thereby interferes with the desired therapeutic function. While the circuit of one present apparatus includes provision for gradually increasing the current at the beginning of each surge, the slope of the increase or the "ramp-up" time is proportional to the pulse rate. However, this arrangement does not provide effective cushioning of the sensory shock for certain patients and at certain operating conditions. For example, the "ramp-up" time would always be relatively short at a high pulse rate, and at high intensity levels, the application of the full current may be uncomfortably abrupt at the commencement of each surge.

It is accordingly an object of the present invention to provide a therapeutic apparatus which is adapted to provide electrical stimulation to the human body, and which effectively overcomes the above noted disadvantages and deficiencies of the present apparatus of this type.

It is a more particular object of the present invention to provide a therapeutic apparatus of the described type which includes a pair of operative electrodes for alternately applying current to the body at spaced points, and which includes means for effectively balancing the current between the two electrodes.

It is also an object of the present invention to provide a therapeutic apparatus of the described type which has provision for monitoring and visibly displaying to the therapist the effectiveness of the treatment, and such that the therapist need not rely on the reaction of the patient.

It is still another object of the present invention to provide a therapeutic apparatus of the described type which has provision for operating in a surge mode wherein pulsed current is intermittently applied, and wherein the initial current at the beginning of each surge is gradually increased, and the rate of increase is adjustable by the therapist so as to minimize shock to the patient, even at high intensity levels, and to permit the application of the current to be adjusted for the different tolerance levels of different patients.

These and other objects and advantages of the present invention are achieved in the embodiment illustrated herein by the provision of a therapeutic apparatus which comprises a pair of electrodes adapted for operative electrical contact with the body of a patient, and circuit means for supplying a pulsed current to each of the electrodes, and with the circuit preferably also including a timer for alternately directing the current to each electrode for a predetermined time period. The circuit means also includes intensity balance control means for permitting the therapist to selectively increase or decrease the current flowing to one electrode with respect to the current flowing to the other electrode. Preferably, the intensity balance control means includes voltage attenuation means in association with each electrode, and such that changes in the voltage will result in a proportional change in the current, and without changing the impedance of the circuit, which would interfere with the desired current measurement as further described below.

As a further aspect of the present invention, it has been discovered that the peak current value of the pulsating current provides a highly effective means for monitoring the effectiveness of the treatment. For example, in terms of muscle contraction, it has been found that the most effective treatment is achieved at high peak current levels, which are achieved at low impedance points on the body. The peak current value is highly responsive to changes in body impedance, as compared to the voltage or average current, and with the present invention, means are provided for continuously monitoring and visibly displaying the peak current value of the pulsed current produced by the circuit means. Thus the operator may locate the most effective treatment points on the body by manually moving the electrode from point to point on the body, while visually observing the peak current at each point.

The preferred embodiment of the present invention also incorporates a circuit for supplying interrupted surges of the pulsed current to each electrode, and which further includes adjustable control means for adjustably selecting the duration of each surge, and the duration of the interval between surges. Further, the circuit includes function generator means for gradually increasing the current intensity from zero to a predetermined maximum intensity at the beginning of each surge, and for adjustably controlling the rate of such increase in the current intensity, with the rate of increase being a function of the selected duration of each surge. By this arrangement, a suitable adjustment for the different tolerance levels of different patients may be readily effected, and thus any discomfort to the patient from the initial application of the current at the commencement of each surge may be effectively alleviated.

Some of the objects and advantages of the invention having been stated, others will appear as the description proceeds, when taken in connection with the accompanying drawings, in which FIG. 1 is a perspective view of a therapeutic apparatus embodying the features of the present invention;

FIG. 2 is a front plan view of the control panel on the apparatus shown in FIG. 1;

Figure 3:
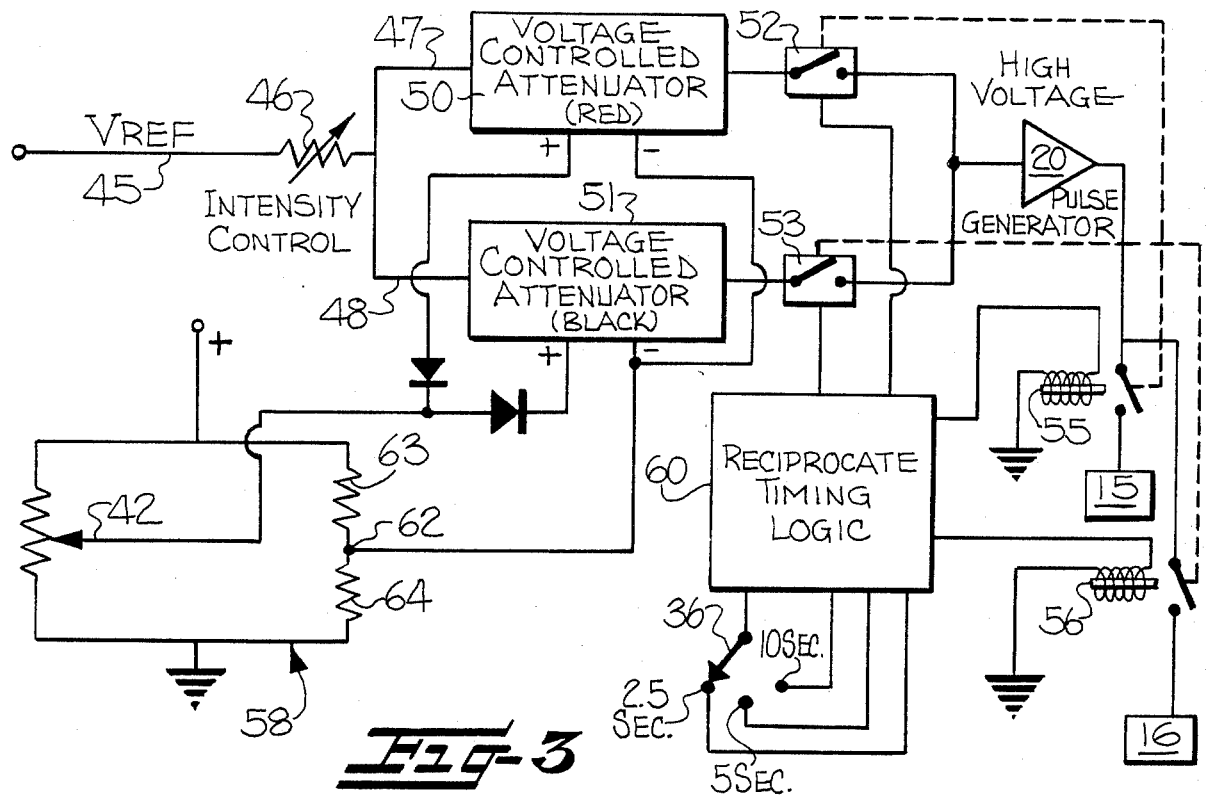
FIG. 3 is a schematic representation of an intensity balance control circuit in accordance with the present invention.

Referring more particularly to the drawings, FIG. 1 illustrates generally at 10 a therapeutic apparatus in accordance with the present invention. In the illustrated embodiment, the apparatus includes a casing 12, to which there is releasably connected a hand held active electrode or probe 14 adapted for point or spot application, and a pair of flat active electrodes 15, 16, each having the form of a rectangular plate which may be about four inches square. The electrode 15 is designated by the color red, and the electrode 16 is designated by the color black. Further, there is provided a relatively large flat indifferent electrode 18 which serves as a dispersive ground for the active electrodes.

The casing 12 of the apparatus mounts a front control panel 19, and houses an electrical pulse generator for supplying a pulsed current to the selected electrode. The pulse generator is shown schematically at 20 in FIGS. 3–5, and is of conventional known design. The current typically has a waveform consisting of adjacent or twin pulses as shown in FIG. 6, and is characterized by relatively high voltage, high peak but low average current, and very short pulse duration. The short duration of the pulses results in an inherently low power output, and no significant heat is generated in the electrodes.

In the illustrated embodiment, the control panel 19 includes an intensity control knob 22 which permits the therapist to selectively adjust the voltage to a level between about 1 to 500 volts, and in normal operation, the peak current ranges between about 50 to 400 milliamps. The duration of each pulse (measured at half peak height) is typically between about 15 to 30 microseconds when measured with a load impedance of 1000 ohms, it being understood that the pulse width will vary with the impedance of the patient's body. There is typically about 75 microseconds between the pulses of each pair, and the total duration of each pair of adjacent pulses is on the order of about 100 microseconds. The frequency of the twin pulses is controlled by the knob 24 in a range of between about 1 to 120 twin pulses per second, and a light 25 is positioned adjacent the knob 24 which is lighted with each pulse to visually indicate the pulse rate.

Figure 7:
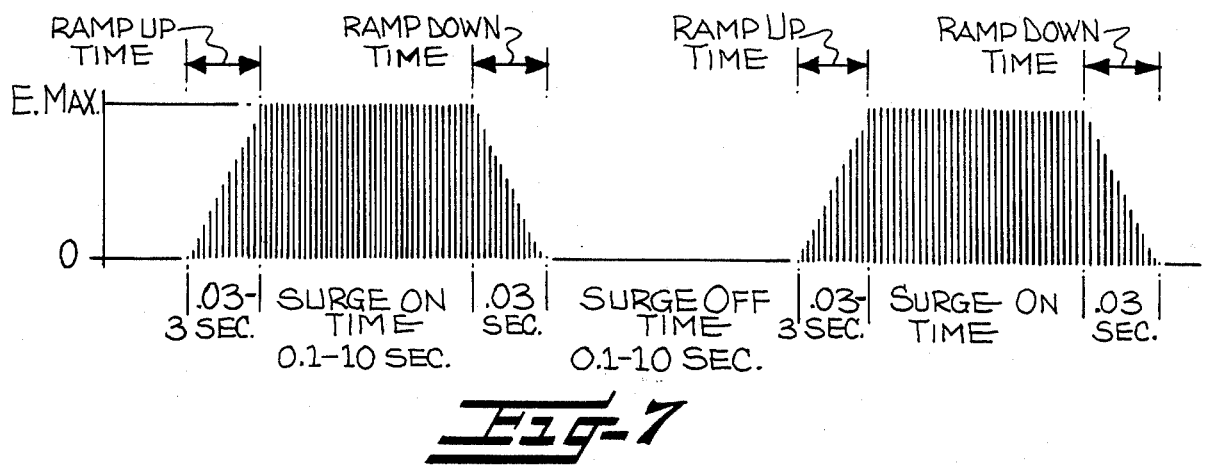
FIG. 7 is a current-time graph illustrating the current waveform in the intermittent or surge mode of operation.

The control panel 19 further mounts a master on-off power switch 26, a master timer for permitting the total treatment time to be selected, and a meter 30 for visually displaying either the voltage or current (peak milliamps) as selected by the output switch 31. Moving the output switch 31 to one position causes the meter 30 to display the voltage and to light the voltage readout indicator 32, and moving the switch 31 to the other position causes the meter 30 to display the peak current and to light the current readout indicator 34. Further, there is provided a polarity selector 35 for selecting either a positive or negative polarity for the pair of electrodes, and a function selector switch 36 for selecting the mode of operation. Specifically, the selector switch 36 permits selection between the hand held probe 14 and the pair of electrodes 15, 16. When the selector 36 is in the "probe" position the output is operatively connected to the probe 14 and in continuous operation. In the "continuous", "surge", and "reciprocate" positions, the output is operatively connected to the pair of electrodes 15, 16. In "continuous" mode, the electrodes are on continuously, in "surge" mode, both electrodes are cycled on and off together at rates selected by the surge-on control dial 38 and surge-off control dial 40, and in the manner illustrated in FIG. 7 (wherein each vertical line represents a twin pulse). A light 41 is provided on the control panel adjacent the surge-on dial 38 which is lighted when an output is being applied.

The "reciprocate" mode involves three selectable time periods, namely 2.5, 5 and 10 seconds. These three positions determine the time that one electrode is on while the other is off, and at the selected interval, the electrode that is on will switch off and the electrode that is off will switch on. This alternate switching continues throughout the total treatment time as set by the master timer.

Any time the selector switch 36 is moved, a safety circuit (not shown) is provided which terminates the output. The output will remain at zero until the apparatus is reset, by rotation of the intensity control knob 22 to zero. Thus the intensity will always commence at zero with the commencement of any treatment mode.

The control panel 19 further mounts an intensity balance knob 42 which is operable in the "reciprocate" mode as hereinafter further described, and a pair of indicator lights 43, 44 respectively designated red and black for visually indicating which of the pair of electrodes 15, 16 is operatively connected to the circuit.

FIG. 3 illustrates an intensity balance circuit adapted for use with the present invention when operated in the "reciprocate" mode. In the illustrated embodiment, a reference voltage is applied in the line 45 which includes the intensity control 46 which is adjusted by the intensity knob 22. The voltage is then fed into the parallel branch lines 47, 48. A separate voltage controlled attenuator 50, 51 is positioned in each of the branch lines, together with an associated solid state switch 52, 53. The two branch lines then join and pass through the conventional pulse generator 20 which produces a high voltage pulsed current as described above. The output of the generator is directed to a pair of relays 55, 56 which are respectively connected to the electrodes 15 and 16.

The intensity balance circuit further includes a bridge network 58, which is operatively connected to the intensity balance control knob 42 on the control panel, and the bridge network is operatively connected to each of the voltage controlled attenuators 50, 51. A reciprocate timing and switching logic circuit 60 controls the two solid state switches 52, 53, and incorporates the reciprocate timing portion of the switch 36 mounted on the control panel of the apparatus. The circuit 60 further controls the pair of relays 55, 56 for selectively activating the electrodes 15, 16, concurrently with the closing of the associated solid state switch 52, 53.

In operation, the intensity balance control knob 42 is initially placed in the middle of its rotation, and the bridge is thus balanced such that there is no output from the bridge. If the knob 42 is turned clockwise, the wiper of the control moves upwardly as seen in FIG. 3 and becomes more positive than the juncture 62 between the two resistors 63, 64 causing the attenuator 51 in the black line to increase its attenuation and thus decrease its voltage, while the attenuation in the red line is unchanged. If the knob 42 is turned counterclockwise, the wiper becomes more negative than the resistor junction 62, causing the red line attenuator 50 to increasingly attenuate the intensity level, while that in the black line is unchanged. The reciprocate timing logic 60 alternately interconnects the red electrode and the black electrode to the output circuit, concurrently with the closure of the associated switches 52, 53.

The changes in voltage from the attenuators will result in a proportional change in current to the associated electrodes. Thus the illustrated voltage attenuation circuit permits the therapist to selectively increase or decrease the current flowing to one electrode with respect to the current flowing to the other electrode. Further, the current may be changed without changing the impedance of the circuit, which would interfere with the measurement of the peak current to the body, and the circuit will maintain a low impedance as compared to the impedance of the patient's body, to thereby permit accurate measurement of the peak current to the body.

Figure 4:
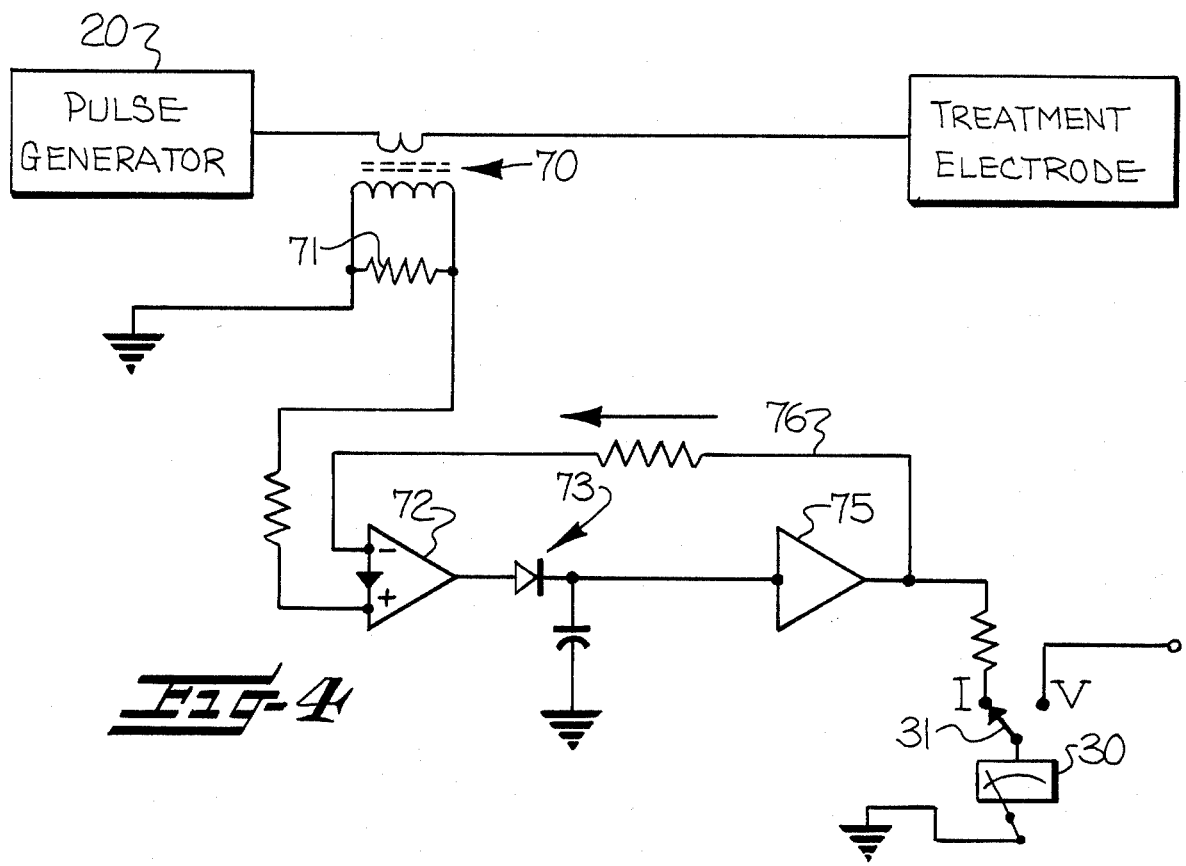
FIG. 4 is a schematic representation of a peak current measuring circuit in accordance with the present invention.

FIG. 4 illustrates a circuit for continuously monitoring and visually displaying the peak current value of the pulsed current flowing from the generator 20. In the illustrated embodiment, the circuit includes a current transformer 70 having an associated shunt 71, which develops a voltage that is proportional to the current flowing to the electrode. The transformer also serves to isolate the circuit from the patient for safety purposes. A wide band amplifier 72 amplifies the output of the current transformer by for example a factor of forty, and then feeds the large output to the diode capacitor network 73. The diode acts to charge the capacitor to the peak voltage from the wide band amplifier. The buffer 75 provides an output that is the same as the voltage to which the capacitor is charged, and this output, which is proportional to the peak current, is displayed on the control panel meter 30 when the switch 31 is moved to the amperage readout position. The output is also fed back in line 76 to the wide band amplifier to compensate for nonlinearities in the diode and to control the gain of the wide band amplifier. The display meter 30 includes a pivotally mounted needle, and the needle movement follows the output of the buffer 75 for limiting the rapid movement thereof.

Figure 5:
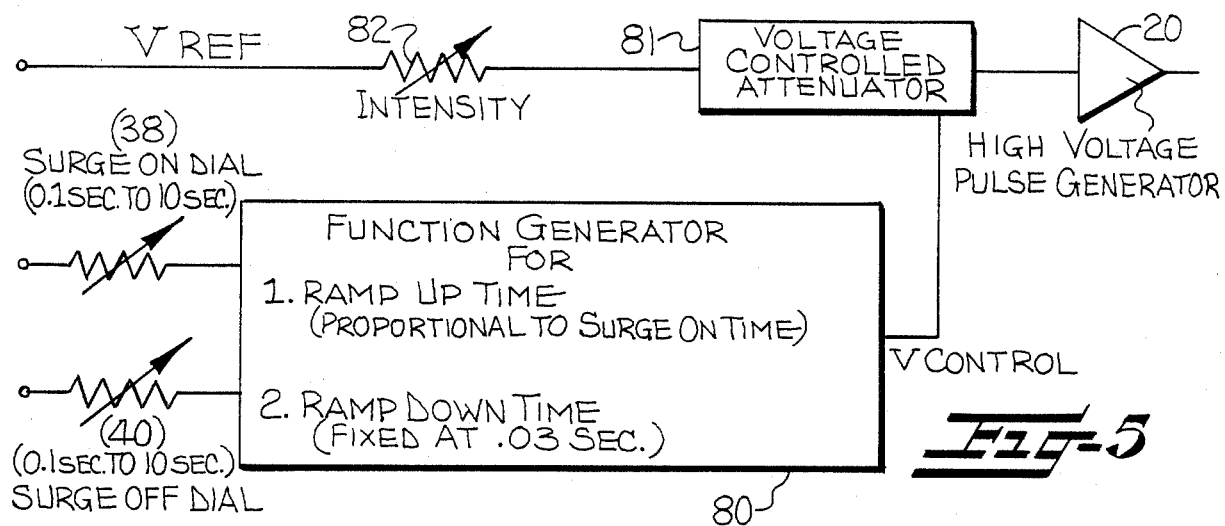
FIG. 5 is a schematic representation of a surge control circuit in accordance with the present invention.
Figure 6:
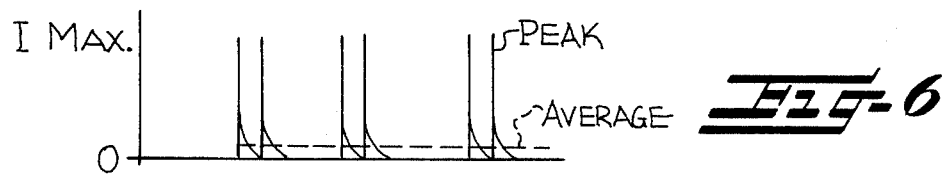
FIG. 6 is a current-time graph illustrating a current waveform adapted for use with the present invention.

A preferred embodiment of a surge control circuit is illustrated schematically in FIG. 5, and is composed of a function generator 80 and a voltage controlled attenuator 81 which modulates a reference voltage which controls the high voltage pulse generator 20. The function generator 80 produces a control voltage output with four controlled functions, namely, the surge-on time as determined by the setting of the dial 38 on the control panel, the surge-off time as determined by the setting of the dial 40, the ramp-up time and the ramp-down time, note FIG. 7. As illustrated, the surge-on dial 38 and the surge-off dial 40 each have a control variable from 0.1 to 10 seconds. Also, by conventional circuit design, the ramp-up time is proportional to the surge-on time, and the ramp-down time is fixed at 0.03 seconds. The control voltage from the function generator 80 is fed to the voltage controlled attenuator 81, which modulates the voltage determined by the variable intensity control 82, which is controlled by the knob 22 on the control panel. The modulated voltage in turn controls the output voltage of the pulse generator 20 from zero to the preset maximum intensity.

In the illustrated embodiment, the ramp-up time is about one third of the surge-on time as set by the dial 38. Thus the therapist may effectively cushion the sensory shock to the patient at the commencement of each surge, by extending the surge-on time to thereby lengthen the ramp-up time. Further, such tieing of the ramp-up time to the surge-on time permits effective control without the use of additional dials on the control panel.

In the drawings and specification, there has been set forth a preferred embodiment of the invention, and although specific terms are employed, they are used in a generic and descriptive sense only and not for purposes of limitation.

That which is claimed is:

1. A therapeutic apparatus for applying electrical stimulation to at least two spaced points on the body of a patient, and having the ability to balance the stimulation felt by the patient at two of the spaced points, and comprising a pair of electrodes adapted for operative electrical contact with the body of the patient, circuit means operatively connected to each of said electrodes for supplying a pulsed current thereto, with the current being characterized by relatively high voltage, high peak but low average current, and very short pulse duration, said circuit means including intensity balance means for selectively increasing or decreasing the current flowing to one electrode with respect to the current flowing to the other electrode, to thereby permit adjustment for different impedances of different parts of the body and permit the patient's sensation from the two electrodes to be balanced, said intensity balance means including separate voltage attenuation means in association with each electrode, and such that changes in the voltage resulting from said voltage attenuation means will result in a change in the current without significantly changing the impendance of said circuit means.

2. The therapeutic apparatus as defined in claim 1 wherein said circuit means includes means for generating a pulsed current having a selectable voltage of between about 1 to 500 volts, and a peak current in normal operation of between about 50 to 400 milliamperes.

3. The therapeutic apparatus as defined in claim 2 wherein said circuit means further includes means for generating a current having a waveform of closely adjacent pairs of pulses, with the duration of each pair being about 100 microseconds, and means for adjusting the frequency of the pairs of pulses in a range between about 1 to 120 per second.

4. The therapeutic apparatus as defined in any one of claims 1-3 wherein said intensity balance means further includes adjustable bridge circuit means operatively connected to each of said voltage attenuation means for selectively changing the attenuation thereof.

5. The therapeutic apparatus as defined in claim 4 further comprising intensity control means for adjustably increasing or decreasing the current flowing to both of the electrodes.

6. The therapeutic apparatus as defined in claim 4 wherein said circuit means further comprises means for continuously monitoring and visibly displaying the peak current value of the pulsed current.

7. The therapeutic apparatus as defined in claim 4 wherein said circuit means further comprises switch means for selectively adjusting the time for directing the current to each electrode.

8. A therapeutic apparatus for applying electrical stimulation to at least two spaced points on the body of a patient, and having the ability to balance the stimulation felt by the patient at two of the spaced points, and comprising a pair of electrodes adapted for operative electrical contact with the body of the patient, current generator means for generating a pulsed current characterized by relatively high voltage, high peak but low average current, and very short pulse duration, an output line from said current generator means and having first output switch means for operatively connecting a first of said pair of electrodes to said generator means, and second output switch means for operatively connecting a second of said pair of electrodes to said generator means, input means for providing a controlled reference voltage to said current generator means to control the magnitude of the current generated thereby, and including a pair of parallel branch lines, voltage attenuation means disposed in each of said branch lines, first branch line switch means disposed in one of said branch lines, and second branch line switch means disposed in the other of said branch lines, control means operatively connected to each of said voltage attenuation means for selectively controlling the attenuation thereof, and timing logic switch means for alternately (1) closing both said first output switch means and first branch line switch means, and (2) closing both said second output switch means and second branch line switch means, whereby the current is alternately directed to each electrode, and the current to each electrode is controlled by an individual one of said voltage attenuation means.

9. The therapeutic apparatus as defined in claim 8 wherein said timing logic switch means includes means for varying the time between the alternating closure of the switch means.

10. The therapeutic apparatus as defined in claim 8 wherein said input means further includes a commom intensity control means connected to each of said branch lines.

11. The therapeutic apparatus as defined in any one of claims 8-10 wherein said control means includes a bridge circuit operatively connected to each of said voltage attenuation means, and such that a change in the output of the bridge circuit acts to increase or decrease the current flowing to one electrode with respect to the current flowing to the other electrode.

12. A therapeutic apparatus for applying electrical stimulation to the body of a patient, characterized by the ability to apply a pulsed current in interrupted surges, and the ability to effectively alleviate any discomfort to the patient from the initial application of the current at the commencement of each surge, said apparatus comprising, at least one electrode adapted for operative electrical contact with the body of the patient, circuit means operatively connected to said one electrode for supplying a pulsed current thereto, with the current being characterized by relatively high voltage, high peak but low average current, and very short pulse duration, adjustable intensity control means operatively connected to said circuit means for selectively setting the intensity of the current flowing to said one electrode, and current control means operatively connected to said circuit means for periodically interrupting the current to produce interrupted surges of pulsed current, and including adjustable control means for adjustably selecting the duration of each surge, and function generator means for gradually increasing the current intensity from zero to a predetermined maximum intensity at the beginnning of each of said surges and for controlling the rate of such increase in the current intensity, with the rate of increase being a function of the selected duration of each surge.

13. The therapeutic apparatus as defined in claim 12 wherein said function generator means further includes means for gradually decreasing the current intensity from the predetermined maximum intensity to zero at the termination of each of said surges.

14. The therapeutic apparatus as defined in claims 12 or 13 wherein said current control means further includes means for adjustably selecting the duration of the interval between surges.

* * * * *